(12) United States Patent
Rosa et al.

(10) Patent No.: US 11,331,092 B2
(45) Date of Patent: May 17, 2022

(54) RETRACTOR

(71) Applicant: MEDACTA INTERNATIONAL SA, Castel San Pietro (CH)

(72) Inventors: Andrea Rosa, Castel San Pietro (CH); Francesco Siccardi, Castel San Pietro (CH); Antonino Romeo, Castel San Pietro (CH); Massimiliano Bernardoni, Castel San Pietro (CH); Christophe Monnin, Marcq-en-Baroeul (FR)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 0 days.

(21) Appl. No.: 17/262,842

(22) PCT Filed: Jul. 16, 2019

(86) PCT No.: PCT/IB2019/056062
§ 371 (c)(1),
(2) Date: Jan. 25, 2021

(87) PCT Pub. No.: WO2020/021385
PCT Pub. Date: Jan. 30, 2020

(65) Prior Publication Data
US 2021/0137510 A1 May 13, 2021

(30) Foreign Application Priority Data
Jul. 25, 2018 (IT) .......................... 102018000007489

(51) Int. Cl.
*A61B 17/02* (2006.01)
*A61B 17/16* (2006.01)

(52) U.S. Cl.
CPC ........ *A61B 17/025* (2013.01); *A61B 17/1684* (2013.01)

(58) Field of Classification Search
CPC .......................... A61B 17/025; A61B 17/1684
(Continued)

(56) References Cited

U.S. PATENT DOCUMENTS

| | | | |
|---|---|---|---|
| 5,133,720 A | 7/1992 | Greenberg | |
| 5,380,331 A * | 1/1995 | Mikhail | ................ A61B 17/02 606/53 |

(Continued)

OTHER PUBLICATIONS

International Search Report and Written Opinion for International Application No. PCT/IB2019/056062 dated Oct. 30, 2019.

*Primary Examiner* — Ellen C Hammond
*Assistant Examiner* — David C Comstock
(74) *Attorney, Agent, or Firm* — Meunier Carlin & Curfman LLC

(57) ABSTRACT

A retractor for surgery according to various implementations comprises a handle, an operating portion, and a curved body. In a side view, the handle, the curved body, and the operating portion each define a mean line, wherein:
- the mean line of the curved body extends along an arc,
- the mean line of the handle is tangent to the arc,
- the mean line of the operating portion defines a concavity opposed to the concavity of the arc;
- the operating portion comprises a retraction segment and one rest segment comprising a tip; and
- the extension of the circular arc intersects the rest segment.

In a front view, the curved body defines an opening comprising a proximal portion having width l and a distal portion having width L, wherein l<L.

16 Claims, 8 Drawing Sheets

(58) Field of Classification Search
USPC .................. 600/210, 217, 235; 606/89, 90; D24/133, 135, 140
See application file for complete search history.

(56) References Cited

U.S. PATENT DOCUMENTS

| | | | |
|---|---|---|---|
| 6,685,632 B1 * | 2/2004 | Hu | A61B 17/0206 600/231 |
| D549,331 S * | 8/2007 | Tomatsu | A61B 17/1642 D24/133 |
| 7,785,255 B2 * | 8/2010 | Malkani | A61B 17/88 600/235 |
| D658,285 S * | 4/2012 | Ryshkus | A61B 17/1714 D24/135 |
| 2004/0172038 A1 * | 9/2004 | Dye | A61B 17/02 606/91 |
| 2009/0012370 A1 * | 1/2009 | Gutierrez | A61B 17/02 600/201 |
| 2011/0106124 A1 * | 5/2011 | Beauchamp | A61B 17/1642 606/170 |
| 2013/0030442 A1 * | 1/2013 | Pilgeram | A61B 17/1714 606/96 |
| 2014/0275792 A1 * | 9/2014 | Hawkins | A61B 5/14542 600/202 |
| 2015/0196289 A1 * | 7/2015 | Ryshkus | A61B 17/025 600/204 |
| 2018/0064547 A1 | 3/2018 | Greiwe | |
| 2021/0128318 A1 * | 5/2021 | Chow | A61B 17/8866 |

* cited by examiner

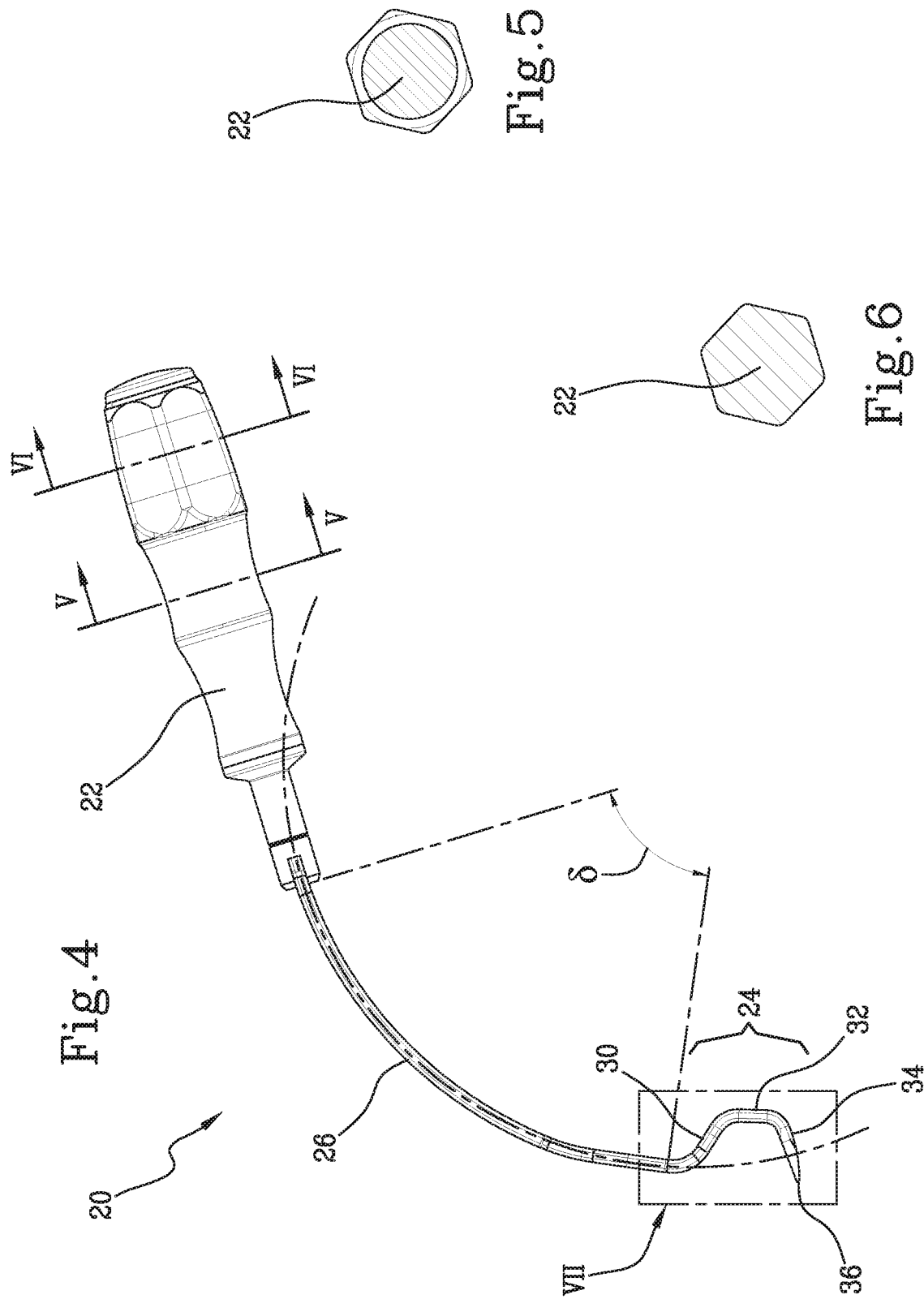

RETRACTOR

The present invention relates to a surgical retractor, in particular a surgical retractor for surgery of the shoulder.

In orthopaedic surgery in general, and surgery of the shoulder in particular, the use is known of retractors to allow the surgeon, once the skin incision has been made, to move the soft tissues laterally so as to expose the portions of bone on which the surgery is to be performed. By way of example, in the implantation of a joint prosthesis, various procedures are necessary in which the soft tissues need to be moved away from the operating field in order to allow an adequate vision of the bones and not to unnecessarily injure the soft tissues themselves.

More specifically, the shoulder prosthesis is intended to replace the head of the humerus on one side and the glenoid cavity (or glena) on the other side with artificial products. For this purpose, the surgeon must prepare both parts to accommodate the two portions of the prosthesis.

Typically, preparation requires that each bone be made regular and shaped to properly accommodate the respective prosthetic part. This is usually done with a specific orthopaedic reamer operated by the surgeon by hand.

Specifically, as regards the preparation of the glena, all the soft tissues surrounding it and the head of the humerus, previously released from the joint, must be temporarily moved aside from the operating field.

In order to move the soft tissues, instruments called retractors are commonly used. Retractors of a known type have a body shaped in such a way as to facilitate the leverage action that they must perform to move the soft tissues aside. The body of the known retractors consists of a single metal sheet suitably shaped to define a handle portion, provided with one or more holes, and a rest portion, provided with one or more tips. The tips of the rest portion are intended to grip the surface of the bone to prevent the retractor from sliding or moving while the surgeon levers it to move the soft tissues. In turn, the holes provided in the handle area allow the surgeon to secure the retractor in position, either by coupling a special traction device or—more often—by inserting a finger into it.

These retractors, although widely used and appreciated, are not without drawbacks. In fact, the curve defined by the retractor body in proximity of the rest portion means that a part of the retractor remains very close to the site where the bone to be reamed is situated. Clearly, with the retractor are also the soft tissues that rest on it and that are therefore very close to the area of use of the reamer. This situation, which arises because of the particular shape of the known retractors, entails a number of risks.

If the surgeon, while using the reamer, leaves the retractor in the position described, then there is a risk that the reamer may cause injury to the surrounding soft tissues and/or that the reamer or the handle thereof may inadvertently touch the retractor body. This involuntary contact implies, in addition to any damage to the device itself, a sudden deviation of the reamer from the desired trajectory and therefore the risk of potential further damage to the surrounding tissues.

To avoid these undesirable eventualities, the surgeon can further displace the soft tissues and retractor itself by forcing the leverage action. This solution implies a state of effort for the surgeon which, although localized, is quite high and often difficult to maintain for as long as necessary. The consequence is often muscle fatigue, which can lead to a limitation of the quality of the surgery. In addition, by arbitrarily forcing the displacement of the soft tissues, the surgeon may inadvertently cause strain to the same.

Lastly, in known retractors, the handle portion made from the metal sheet does not guarantee adequate gripping ergonomics and can easily slide out of the surgeon's hand.

The object of the present invention is therefore to overcome the drawbacks highlighted above in relation to the prior art.

In particular, one task of the present invention is to provide a retractor that allows soft tissues to be moved away from the operating site in an easy and controlled manner.

A further task of the present invention is to provide a retractor that allows easy use of the reamer, avoiding accidental contact with it.

Such purpose and tasks are achieved by a retractor according to claim 1.

For a clearer understanding of the invention and its advantages, some examples of non-limiting embodiments thereof are described below, with reference to the appended drawings, wherein:

FIG. 4 shows another side view of the retractor in FIG. 1;

FIG. 5 shows a view of the cross-section obtained along line V-V in FIG. 4;

FIG. 6 shows a view of the cross-section obtained along line VI-VI in FIG. 4;

Figure 1:
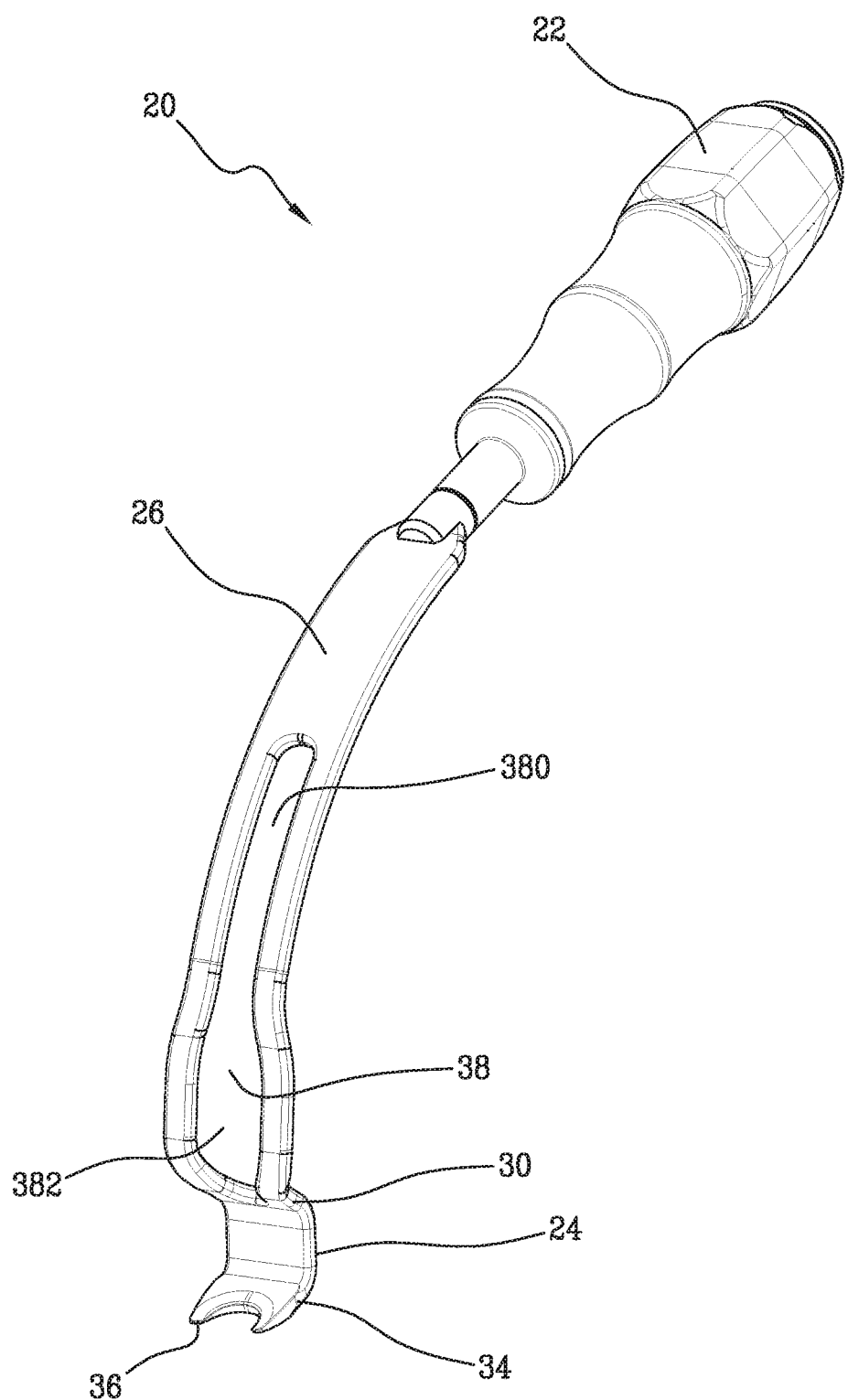
FIG. 1 shows a front-side perspective view of a retractor according to the invention.

The invention relates to a retractor 20 for use in orthopaedic shoulder surgery, comprising a proximal handle 22, a distal operating portion 24, and a curved body 26 connecting the proximal handle 22 to the distal operating portion 24. In a side view of the retractor 20, the handle 22, the curved body 26, and the operating portion 24 each define a respective mean line, wherein:

the mean line of the curved body 26 mainly develops along a circular arc c, the mean line of the handle 22 is tangent to the circular arc c, the mean line of the operating portion 24 is a polyline comprising straight and/or curved segments and defines a concavity opposed to the concavity of the circular arc c;

the operating portion 24 comprises at least one retraction segment 30 and one rest segment 34 comprising at least one tip 36; and the extension of the circular arc c intersects the rest segment 34.

In addition, in a front view of the retractor 20, the curved body 26 defines an elongated opening 38 comprising a first proximal portion 380 having a first width l and a second distal portion 382 having a second width L, wherein l<L.

Within this discussion, some terminological conventions have been adopted in order to make reading easier and simpler. These terminological conventions are clarified below with reference to the appended drawings.

The term "proximal" refers to a position that, in the correct use of the retractor 20, is relatively close to the surgeon. Similarly, the term "distal" refers to a position relatively far from the surgeon.

Figure 3:
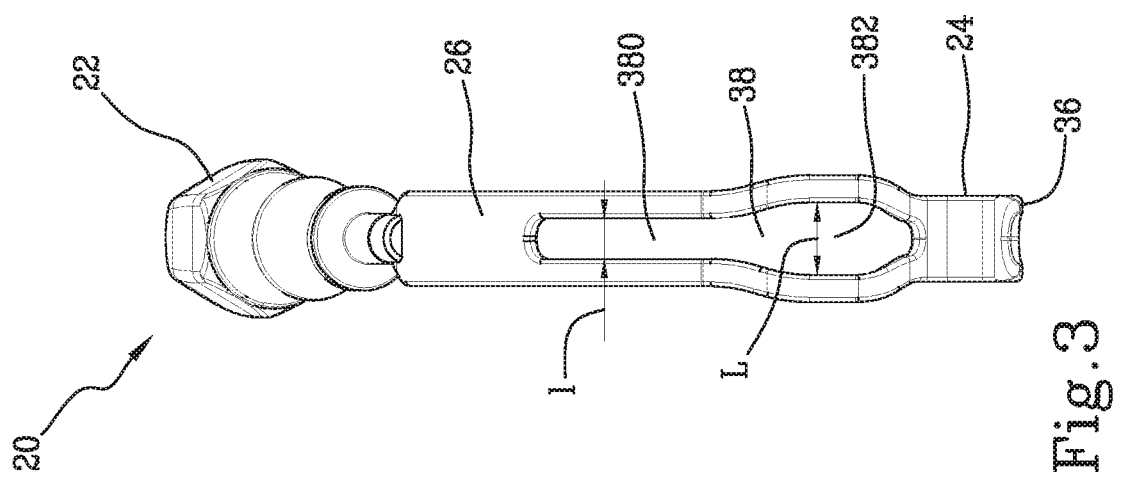
FIG. 3 shows a front view of the retractor in FIG. 1.
Figure 2:
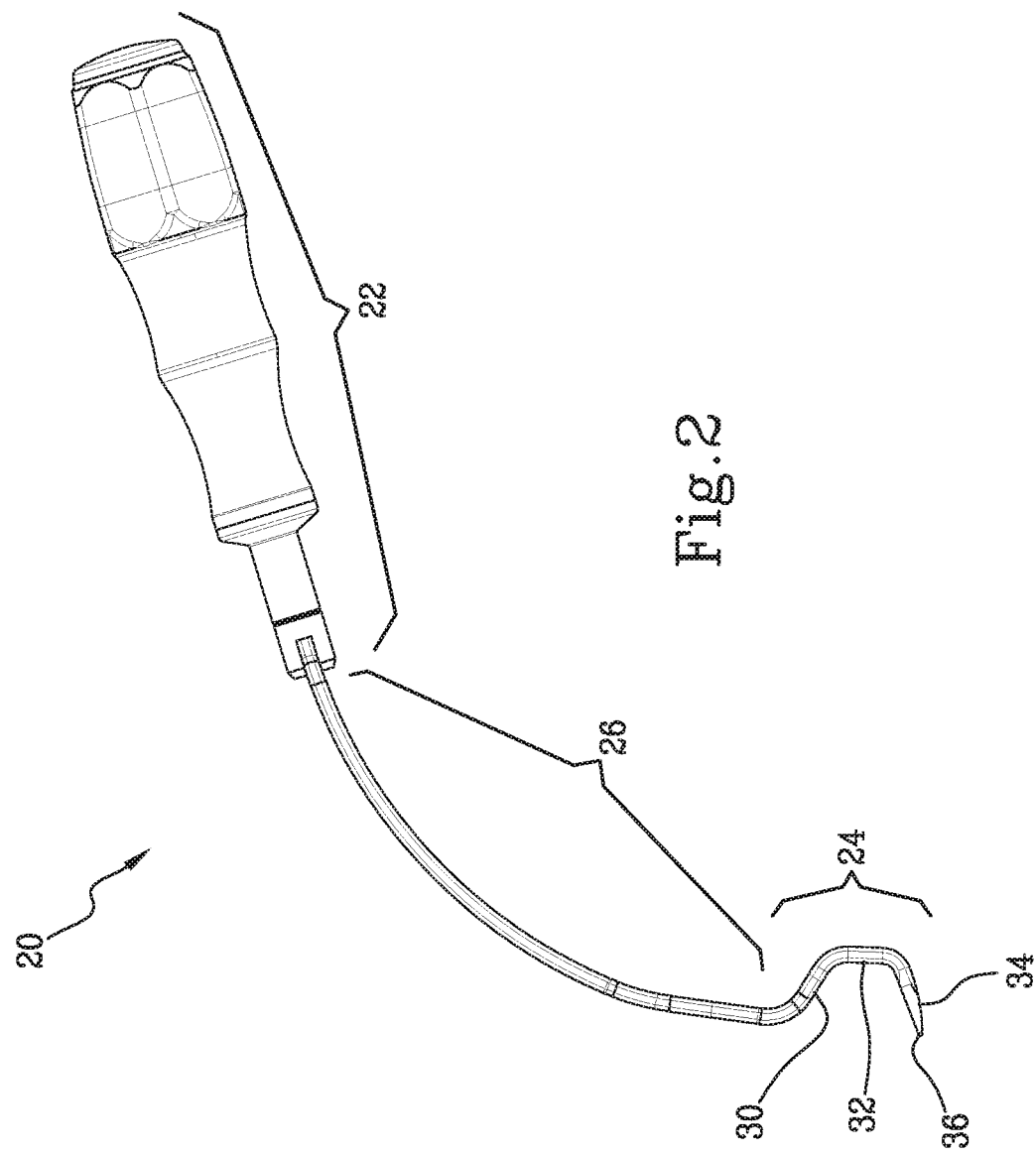
FIG. 2 shows a side view of the retractor in FIG. 1.

Hereinafter, the terms "front", "anterior", "in front of" and the like intuitively refer to the part of the retractor 20 that is within the surgeon's view during use. As the person skilled in the art will clearly understand, the particular shape of the retractor 20 implies that there are actually different directions from which a front view is obtained. For the purposes of this discussion, however, a distinction between the different front views is not necessary. Examples of front views are provided in the attached FIGS. 3 and 8.

As a consequence of the aforesaid, the terms "lateral", "side" and the like mean the part of the retractor 20 viewed from a direction perpendicular to all the directions from which a front view is obtained. Examples of side views are provided in the appended drawings 2, 4 and 7.

Lastly, the terms "rear", "behind" and the like refer to the part of the retractor 20 opposite to the front.

The mean line of the retractor 20 defines overall two different concavities. The first concavity is that of the arc of circumference c which approximates the mean line of the curved body 26. This first concavity, as can be seen in the appended drawings and in view of the conventions adopted in this description, is facing backwards. The second concavity is that defined by the polyline representing the mean line of the operating portion 24. This second concavity, being opposite the first, faces forward.

According to a number of embodiments, the curved body 26 and the operating portion 24 are obtained from a single, suitably shaped, metal sheet. For this reason, it is possible that the distinction between the curved body 26 and the operating portion 24 is not a physical distinction but rather a logical distinction, deriving simply from the different function they perform. By way of example, the boundary between the curved body 26 and the operating portion 24 may be identified where the concavity of the mean line 20 changes direction.

The arc of circumference c approximating the mean line of the curved body 26 preferably has a radius of between 15 cm and 30 cm, even more preferably between 20 cm and 25 cm. Moreover, the same arc of circumference covers an angle δ preferably in the range of 60° to 75°, even more preferably in the range of 65° to 70° (see in this regard FIG. 4).

Figure 11:
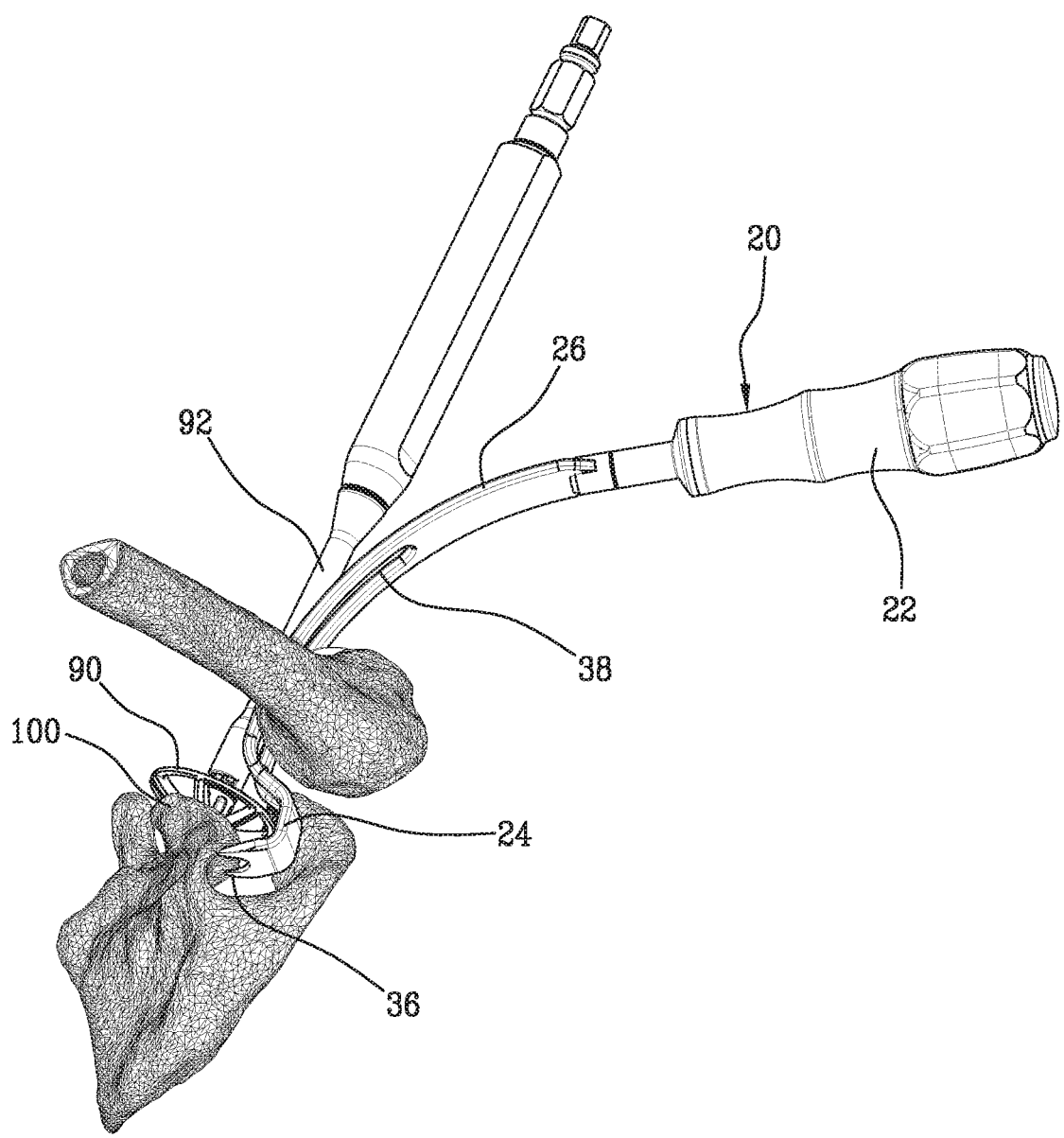
FIG. 11 shows a rear-side perspective view of a retractor according to the invention and of a surgical reamer while operating on the glenoid cavity of a patient.
Figure 12:
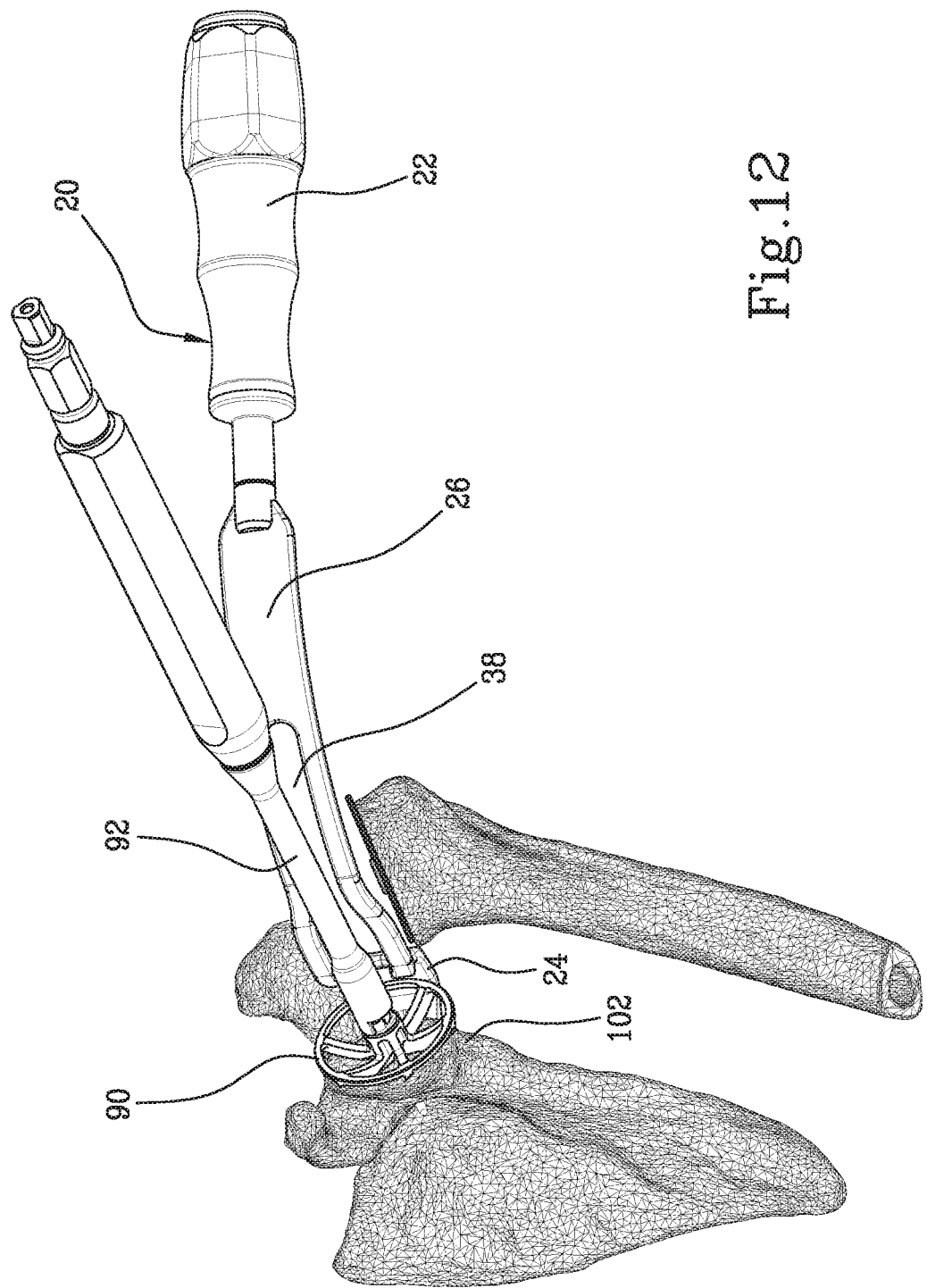
FIG. 12 shows a front-side perspective view of a retractor according to the invention and of a surgical reamer while operating on the glenoid cavity of a patient.

As already mentioned, the operating portion 24 comprises at least one retraction segment 30 and one rest segment 34. The retraction segment 30 branches off the curved body 26 and extends rearwards. The operating portion 24 then comprises a rest segment 34 that is provided with at least one tip 36, preferably two tips 36. The tips 36 are shaped, in a known manner, to grip the surface of the glenoid bone 100 and thereby prevent the retractor 20 from sliding or moving during use. See in this regard FIG. 11 which clearly shows how the tips 36 rest firmly on the back of the glena 100.

Figure 8:
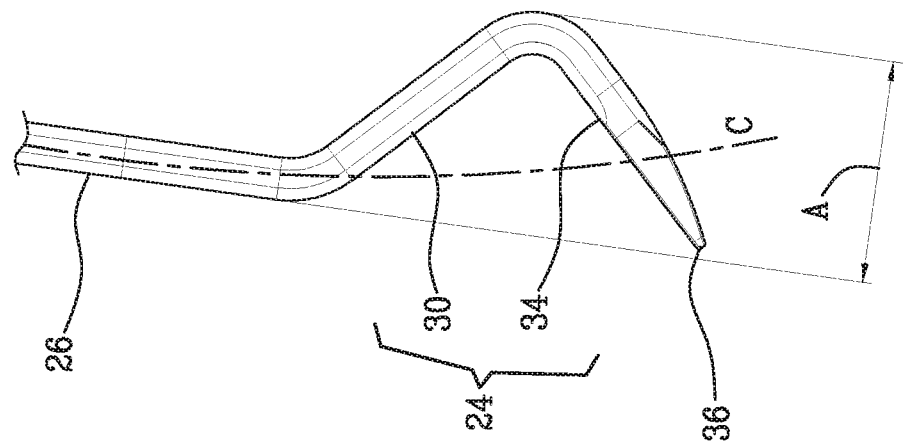
FIG. 8 shows a view similar to that of FIG. 7 of a detail according to a different embodiment of the retractor.

According to some embodiments, the operating portion 24 further comprises an intermediate segment 32 between the retraction segment 30 and the rest segment 34. An embodiment of the retractor 20 in which the operating portion 24 does not comprise the intermediate segment 32 is shown in FIG. 8. Embodiments of the retractor 20 in which the operating portion 24 also comprises the intermediate segment 32 are shown in all the other figures.

Preferably, the retraction segment 30, the rest segment 34 and, if present, the intermediate segment 32 are connected together by curves, so as to avoid corners. Preferably therefore, as a whole, the mean line of the operating portion 24 is a polyline comprising substantially straight parts (the mean lines of the retraction segment 30, the rest segment 34 and, if present, the intermediate segment 32) and decidedly curved parts (the connections between the various segments).

Figure 7:
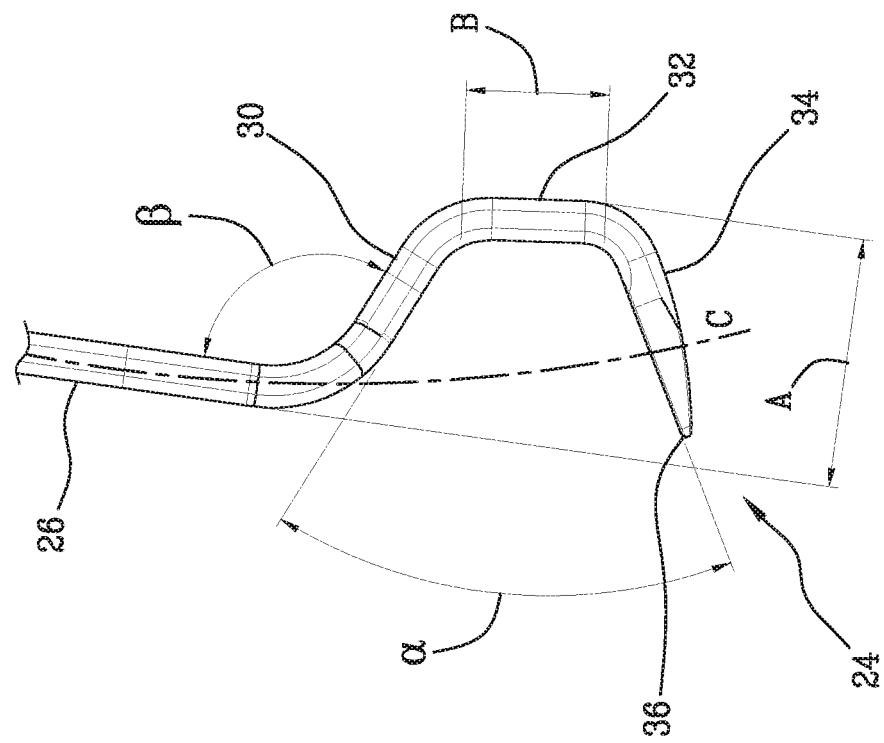
FIG. 7 shows an enlarged view of the detail indicated as VII in FIG. 4.

As can be seen in particular in the embodiment in FIG. 7, the mean line of the retraction segment 30 defines an angle β with the mean line of the distal segment of the curved body 36. The angle β may also be understood as the angle between the mean line of the retraction segment 30 and the tangent to the arc of circumference c in the distal segment of the curved body 36. In particular, the angle β is preferably in the range of 80° to 150°.

Moreover, again with reference to FIG. 7, the mean line of the retraction segment 30 preferably defines an angle α with the mean line of the rest segment 34. In particular, the angle α is preferably in the range of 0° to 90°.

Figure 9:
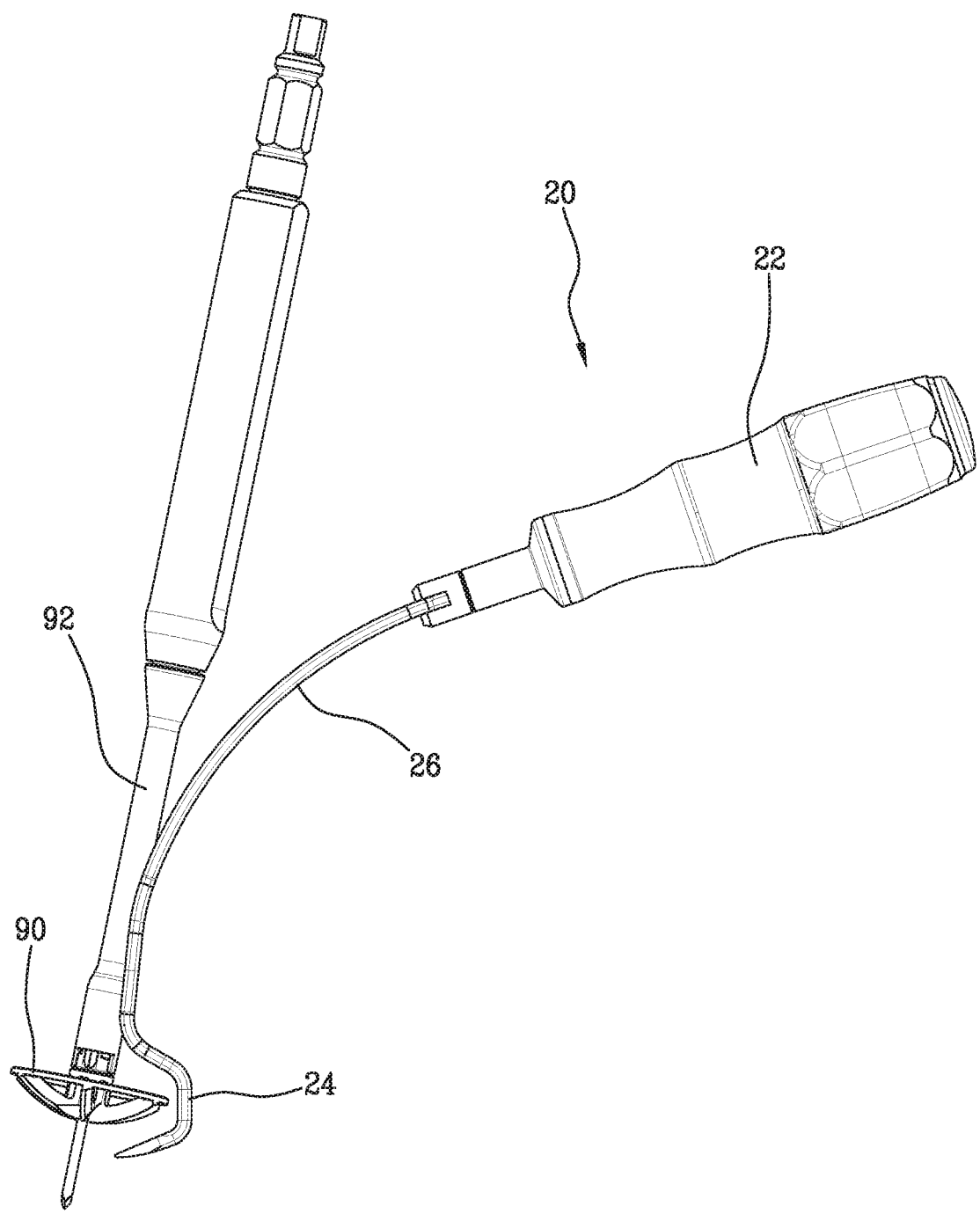
FIG. 9 shows a side view of a retractor according to the invention while acting in conjunction with a surgical reamer.
Figure 10:
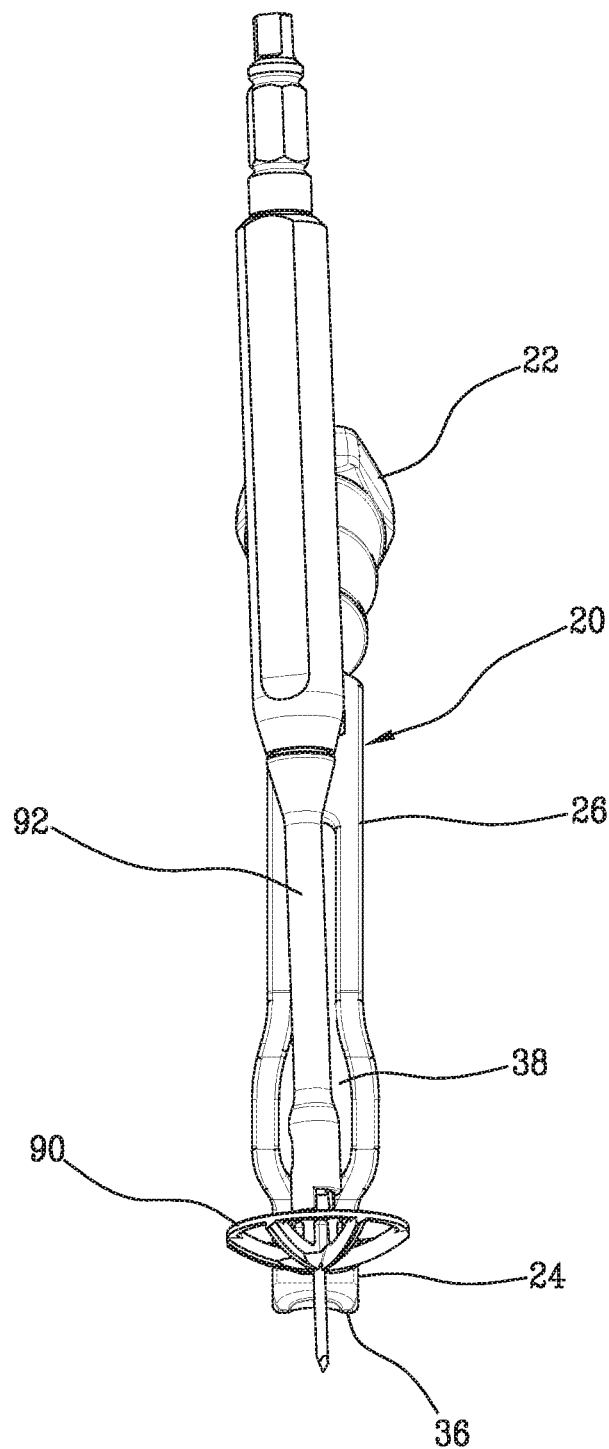
FIG. 10 shows a front view of a retractor according to the invention while acting in conjunction with a surgical reamer.

The retraction segment 30 and thus the entire operating portion 24 extend rearwards from the curved body 26 of the retractor 20. The extent of this rearward extension A is defined below with particular reference to FIGS. 7 and 8. Given the complexity of the shape of the operating portion 24 as a whole, and the possible variants that may be envisaged, in order to provide a unique and repeatable measurement of the rearward extension, A is considered here as the maximum footprint of the operating portion 24 in the direction perpendicular to the curved body segment 26 immediately adjacent. In FIGS. 7 and 8, the measurement A is clearly indicated: it extends between the front tangent to the final segment of the curved body 26 and the rear tangent to the rearmost point of the operating portion 24. Preferably the measurement A is between 8 mm and 35 mm, even more preferably between 20 mm and 30 mm. FIG. 9 clearly shows how the safe use of a reamer 90 depends directly on the measurement A.

FIG. 7 shows an embodiment of the operating portion 24 also comprising the intermediate segment 32 and further shows the measurement B. Preferably the measurement B is between 0 mm and 30 mm, even more preferably between 10 mm and 20 mm. As the person skilled in the art will clearly understand, the particular case in which B equals 0 mm is equivalent to the case shown in FIG. 8 in which the intermediate segment 32 is absent.

As already explained above, the retractor 20 according to the invention also comprises the elongated opening 38. According to some embodiments, the elongated opening 38 extends for more than half of the circumference arc c, from the proximity of the operating portion 24 in a proximal direction towards the handle 22.

Preferably, in a front view, the curved body 26 widens at the second distal portion 382 of the elongated opening 38. In other words, in the proximity of the first proximal portion 380 of the elongated opening 38 the width of the curved body 26 is smaller than the width of the same curved body 26 in the proximity of the second distal portion 382 of the elongated opening 38. Moreover, in the same front view, the width of the rest segment 34 of the operating portion 24 is preferably less than the width of the curved body 26 in the proximity of the second distal portion 382 of the elongated opening 38.

According to the embodiments shown in the appended figures, the handle 22 of the retractor 20 is shaped so as to ensure a firm and easy grip. Preferably the handle 22 is shaped like the handles commonly used for handpieces and hand tools. For example, to ensure a firm and easy grip, the cross section of the handle 22 may be the shape of a circle or polygon circumscribed by a circle. Additionally and/or alternatively, the handle 22 may comprise an outer surface of soft, non-slip material. Materials suitable to constitute the outer surface of the handle 22 may be: silicone, elastomer, natural rubber and the like.

As the person skilled in the art will clearly understand, the invention overcome the drawbacks previously highlighted with reference to the prior art.

In particular, the present invention provides a retractor 20 that allows soft tissues to be moved from the operating site in an easy and controlled manner. In fact, the fact that the operating portion 24 extends rearwards with respect to the curved body 26 of the retractor 20 causes it to move the soft tissues back in a controlled manner. Thanks to the free area created, the surgeon can easily intervene on the glena 100 without any risk of interference with other tissues.

Furthermore, the present invention provides a retractor 20 which, thanks to the elongated opening 38, allows easy use of the reamer 90 and prevents accidental contact with it. The elongated opening 38 and its variable width allow in fact (see in particular FIG. 9) the operation of the reamer 90 in superposition to the curved body 26 of the retractor 20, without thereby making any unwanted contact. The width l of the first proximal portion 380 is sufficient to accommodate the handle 92 of the reamer 90 when the latter is in the operating position. In a more distal position, instead, the second distal portion 382 has a width L greater than l so as to be able to accommodate the movements of said reamer 90. The variable width of the curved body 26, the width of which depends on the width variations of the elongated opening 38, allows the portion of the operating site covered by the retractor itself to be minimized.

It is clear that the specific features are described in relation to various embodiments of the invention by way of non-limiting examples. Obviously, a person skilled in the art may make further modifications and variations to the present invention, in order to meet contingent and specific needs. For example, the technical features described in connection with one embodiment of the invention may be extrapolated therefrom and applied to other embodiments of the invention. Such modifications and variants are also contained within the scope of protection of the invention, as defined by the following claims.

The invention claimed is:

1. A retractor for use in orthopaedic surgery of the shoulder, comprising a proximal handle, a distal operating portion and a curved body connecting the handle to the distal operating portion, wherein, in a side view, the handle, the curved body and the operating portion each define a respective mean line, wherein:

the mean line of the curved body mainly develops along a circular arc having a concavity;
the mean line of the handle is tangent to the circular arc;
the mean line of the operating portion is a polyline comprising straight and/or curved segments and defines a concavity opposed to the concavity of the circular arc;
the operating portion comprises at least one retraction segment and one rest segment comprising at least one tip;
an extension of the circular arc intersects the rest segment; and wherein
in a front view of the retractor, the curved body defines an elongated opening comprising a first proximal portion having a first width l and a second distal portion having a second width L, wherein l<L.

2. The retractor according to claim 1, wherein the circular arc has a radius comprised between 15 cm and 30 cm.

3. The retractor according to claim 2, wherein the radius is between 20 cm and 25 cm.

4. The retractor according to claim 1, wherein the circular arc covers an angle comprised between 60° and 75°.

5. The retractor according to claim 4, wherein the angle is between 65° and 70°.

6. The retractor according to claim 1, wherein the operating portion further comprises an intermediate segment between the retraction segment and the rest segment.

7. The retractor according to claim 6, wherein the retraction segment, the rest segment and the intermediate segment are joined to one another by curves.

8. The retractor according to claim 1, wherein the retraction segment and the rest segment are joined to one another by a curve.

9. The retractor according to claim 1, wherein the mean line of the retraction segment defines an angle with the mean line of the distal portion of the curved body and wherein the angle is comprised between 80° and 150°.

10. The retractor according to claim 1, wherein the mean line of the retraction segment defines an angle with the mean line of the rest segment and wherein the angle is comprised between 0° and 90°.

11. The retractor according to claim 1, wherein the operating portion develops rearward with respect to the curved body by a measure A, wherein A is comprised between 8 mm and 35 mm.

12. The retractor according to claim 1, wherein the elongated opening extends for more than a half of the circular arc.

13. The retractor according to claim 1, wherein, in a front view, the width of the curved body in proximity of the first proximal portion of the elongated opening is smaller than the width of the curved body in proximity of the second distal portion of the elongated opening.

14. The retractor according to claim 1, wherein, in a front view, the width of the rest segment of the operating portion is smaller than the width of the curved body in proximity of the second distal portion of the elongated opening.

15. The retractor according to claim 1, wherein the cross section of the handle has the shape of a circle or of a circumscribed polygon.

16. The retractor according to claim 1, wherein the handle comprises an external surface made of a soft and non-slip material.

* * * * *